United States Patent

Heasman et al.

(10) Patent No.: US 10,292,644 B2
(45) Date of Patent: May 21, 2019

(54) AUTOMATED INNER EAR DIAGNOSES

(71) Applicant: Cochlear Limited, Macquarie University, NSW (AU)

(72) Inventors: John Michael Heasman, Hampton (AU); Peter Gibson, South Coogee (AU); Luke Campbell, Melbourne (AU); Stephen O'Leary, Melbourne (AU)

(73) Assignee: Cochlear Limited, Macquarie University (AU)

( * ) Notice: Subject to any disclaimer, the term of this patent is extended or adjusted under 35 U.S.C. 154(b) by 196 days.

(21) Appl. No.: 15/187,896

(22) Filed: Jun. 21, 2016

(65) Prior Publication Data

US 2017/0360365 A1 Dec. 21, 2017

(51) Int. Cl.
*A61N 1/00* (2006.01)
*A61B 5/00* (2006.01)
(Continued)

(52) U.S. Cl.
CPC .............. *A61B 5/4836* (2013.01); *A61B 5/04* (2013.01); *A61B 5/04001* (2013.01); *A61B 5/12* (2013.01); *A61B 5/125* (2013.01); *A61B 5/6817* (2013.01); *A61B 5/746* (2013.01); *A61N 1/0541* (2013.01); *A61N 1/36038* (2017.08); *H04R 25/70* (2013.01); *H04R 25/554* (2013.01);
(Continued)

(58) Field of Classification Search
CPC .. A61B 5/04; A61B 5/12; A61B 5/746; A61B 5/4836; A61N 1/0541; A61N 1/36036; A61N 1/36038
See application file for complete search history.

(56) References Cited

U.S. PATENT DOCUMENTS 7,137,946 B2 11/2006 Waldmann
8,712,514 B2 4/2014 Nicol et al.
(Continued)

FOREIGN PATENT DOCUMENTS

WO 0052963 A1 9/2000
WO 2013142844 A1 9/2013

OTHER PUBLICATIONS

Campbell, et al., "Cochlear Response Telemetry: Intracochlear Electrocochleography via Cochlear Implant Neural Response Telemetry Pilot Study Results," Otology & Neurotology, Inc., vol. 36, No. 3, Mar. 2015, pp. 399-405.
(Continued)

*Primary Examiner* — Mallika D Fairchild
(74) *Attorney, Agent, or Firm* — Edell, Shapiro & Finnan, LLC (57) ABSTRACT

An expert diagnosis system integrated in a hearing prosthesis system is configured to diagnosis, grade, and remediate inner ear crises. In particular, the expert diagnosis system analyzes combinations of in-situ measured inner ear potentials, obtained in response to electrical and/or acoustic stimulation, in order to identify crisis signatures and to correlate those crisis signatures to clinical symptoms of a specific type and cause of an inner ear crises (i.e., automatically diagnosis the inner ear crisis). The expert system is further configured to grade the severity of the identified clinical symptoms and initiate some form of remedial action to address the identified inner ear crisis.

24 Claims, 6 Drawing Sheets

(51) Int. Cl.
| | |
|---|---|
| A61B 5/04 | (2006.01) |
| A61B 5/12 | (2006.01) |
| A61N 1/05 | (2006.01) |
| H04R 25/00 | (2006.01) |
| A61N 1/36 | (2006.01) |

(52) U.S. Cl.
CPC .......... *H04R 25/558* (2013.01); *H04R 25/606* (2013.01); *H04R 2225/55* (2013.01); *H04R 2225/67* (2013.01)

(56) References Cited

U.S. PATENT DOCUMENTS

| | | | | |
|---|---|---|---|---|
| 2005/0107844 | A1* | 5/2005 | Van Den Honert | ........................ A61N 1/36036 607/57 |
| 2011/0313309 | A1* | 12/2011 | Nicol | ................. A61B 5/04845 600/544 |
| 2012/0143283 | A1 | 1/2012 | Polak | |
| 2012/0191161 | A1 | 7/2012 | van Dijk | |
| 2014/0094712 | A1 | 4/2014 | Buchman et al. | |
| 2015/0057714 | A1 | 2/2015 | Litvak et al. | |

OTHER PUBLICATIONS

Brown, et al., "Estimating the Operating Point of the Cochlear Transducer using Low-frequency Biased Distortion Products," The Journal of the Acoustical Society of America, vol. 125, No. 4, Apr. 2009, pp. 2129-2145.

McClellan, et al., "Round Window Electrocochleography and Speech Perception Outcomes in Adult Cochlear Implant Subjects: Comparison with Audiometric and Biographical Information," Otology & Neurotology, vol. 35, No. 9, Oct. 2014, pp. e245-e252.

Choudhury, et al., "Intraoperative Round Window Recordings to Acoustic Stimuli from Cochlear Implant Patients," NIH Public Access, Author Manuscript, Dec. 2013, 19 pages.

Ferraro, "Electrocochleography: a review of recording approaches, clinical applications, and new findings in adults and children," Journal of the American Academy of Audiology, 21(3), Nov. 3, 2010, pp. 145-152.

Ferraro, et al., "Electrocochleography in the Evaluation of Patients with Meniere's Disease/Endolymphatic Hydrops," Journal of the American Academy of Audiology, vol. 17, No. 1, Jan. 2006, pp. 45-68.

Fitzpatrick, et al. "Round window electrocochleography just prior to cochlear implantation: relationship to word recognition outcomes in adults," HHS Public Access, Author Manuscript, May 2015, 9 pages.

Harris, et al, "Preliminary Results and Technique for Electrophysiological Intra-operative Monitoring of Residual Hearing during Cochlear Implantation," Cochlear Implants International, vol. 12, No. 4, 2011, pp. 209-215, published online Jul. 2013.

Kujawa, et al, "Adding Insult to Injury: Cochlear Nerve Degeneration after "Temporary" Noise-induced Hearing Loss," The Journal of Neuroscience, Nov. 11, 2009, 29(45), pp. 14077-14085.

Mandala, et al., "Electrocochleography during Cochlear Implantation for Hearing Preservation", Otolaryngology—Head and Neck Surgery, vol. 146, No. 5, May 2012, pp. 774-781.

Nourski, et al, "Acoustic-electric Interactions in the Guinea Pig Auditory Nerve: Simultaneous and Forward Masking of the Electrically Evoked Compound Action Potential," Hearing Research, vol. 232, Oct. 2007, pp. 87-103.

Ferraro, et al., "Clinical Electrocochleography," The Hearing Journal, Nov. 1985, pp. 51-55.

Weiss, et al., "A model for signal transmission in an ear having hair cells with free-standing stereocilia. IV. Mechanoelectric transduction stage," Hearing Research, vol. 20, Issue 2, Nov. 1985, pp. 175-195.

Zhang, et al., "Cochlear Dead Regions Constrain the Benefit of Combining Acoustic Stimulation with Electric Stimulation," Ear & Hearing, vol. 35, No. 4, Jul.-Aug. 2014, pp. 410-417.

Schoonhoven, et al., "Response Thresholds in Electrocochleography and Their Relation to the Pure Tone Audiogram," Ear & Hearing, vol. 17, No. 3, Jun. 1996, pp. 266-275.

International Search Report and Written Opinion in counterpart International Application No. PCT/IB2017/053476, dated Aug. 23, 2017.

Luke Campbell, et al., "Cochlear Response Telemetry: Intracochlear Electrocochleography via Cochlear Implant Neural Response Telemetry Pilot Study Results," Otology & Neurotology, Inc., vol. 36, No. 3, 2015, pp. 399-405.

Daniel J. Brown, et al., "Estimating the Operating Point of the Cochlear Transducer using Low-frequency Biased Distortion Products," The Journal of the Acoustical Society of America, vol. 125, No. 4, 2009, pp. 2129-2145, http://doi.org/10.1121/1.3083228.

Joseph H. McClellan, et al., "Round Window Electrocochleography and Speech Perception Outcomes in Adult Cochlear Implant Subjects: Comparison with Audiometric and Biographical Information," Otoloyg & Neurotology, Inc., vol. 35, No. 9, 2014, pp. e245-e252.

Baishakhi Choudhury, et al., "Intraoperative Round Window Recordings to Acoustic Stimuli from Cochlear Implant Patients," NIH PA Author Manuscript, vol. 33, No. 05, pp. 1507-1515, http://doi.org/10.1097/MAO.0b013e31826dbc80.Intraoperative.

John A. Ferraro, "Electrocochleography: a review of recording approaches, clinical applications, and new findings in adults and children," Journal of the American Academy of Audiology, 21(3), Nov. 3, 2010, 145-152, http://doi.org/10.3766/jaaa.21.3.2.

John A. Ferraro, et al., Electrocochleography in the Evaluation of Patients with Meniere's Disease/Endolymphatic Hydrops. Journal of the American Academy of Audiology, 68, vol. 17, No. 1, 2006, pp. 45-68, Retrieved from http://www.ingentaconnect.com/content/aaa/jaaa/2006/00000017/00000001/art00006.

Fitzpatrick, Douglas C., et al. "Round window electrocochleography just prior to cochlear implantation: relationship to word recognition outcomes in adults." Otology & neurotology: official publication of the American Otological Society, American Neurotology Society [and] European Academy of Otology and Neurotology 35.1 (2014): 64.

Robert Harris, et al, "Preliminary Results and Technique for Electrophysiological Intra-operative Monitoring of Residual Hearing during Cochlear Implantation," Cochlear Implants International, vol. 12, No. 4, 2011, pp. 209-215, http://doi.org/10.1179/146701011X12950038111657.

Sharon Kujawa, et al, "Adding Insult to Injury: Cochlear Nerve Degeneration after "Temporary" Noise-induced Hearing Loss," The Journal of Neuroscience: The Official Journal of the Society for Neuroscience, vol. 29, No. 45, 2009, pp. 14077-14085, http://doi.org/10.1523/JNEUROSCI.2845-09.2009.

Marco Mandala, et al., "Electrocochleography during Cochlear Implantation for Hearing Preservation", Otolaryngology—Head and Neck Surgery, vol. 146, No. 5, 2012, http://doi.org/10.1177/0194599811435895.

Kirill V. Nourski, et al, "Acoustic-electric Interactions in the Guinea Pig Auditory Nerve: Simultaneous and Forward Masking of the Electrically Evoked Compound Action Potential," Hearing Research, vol. 232, pp. 87-103, 2007, http://doi.org/10.1016/j.heares.2007.07.001.

John A. Ferraro, et al., "Clinical Electrcochleography," The Hearing Journal, Nov. 1985, pp. 51-55.

T. F. Weiss, et al., A Model for Signal Transmission in an Ear Having Hair Cells with Free-standing Stereocilia. IV. Mechanoelectric Transduction Stage, Hearing Research, vol. 20, No. 2, 1985, pp. 175-195. http://doi.org/10.1016/0378-5955(85)90167-4.

Ting Zhang, et al., Cochlear Dead Regions Constrain the Benefit of Combining Acoustic Stimulation with Electric Stimulation. Ear & Hearing, vol. 35, No. 4, pp. 410-417, 2014, http://doi.org/10.1097/AUD.0000000000000032.

* cited by examiner

AUTOMATED INNER EAR DIAGNOSES

BACKGROUND

Field of the Invention

The present invention relates generally to hearing prostheses.

Related Art

Hearing loss, a type of sensory impairment that may be due to many different causes, is generally of two types, conductive and/or sensorineural. Conductive hearing loss occurs when the normal mechanical pathways of the outer and/or middle ear are impeded, for example, by damage or obstruction to the ossicular chain or ear canal. Sensorineural hearing loss occurs when there is damage to the inner ear, or to the nerve pathways from the inner ear to the brain.

Individuals who suffer from conductive hearing loss typically have some form of residual acoustic hearing (residual hearing) because the hair cells in the cochlea are undamaged. As such, individuals suffering from conductive hearing loss typically receive an auditory prosthesis that generates pressure changes in the cochlea fluid. Such auditory prostheses include, for example, acoustic hearing aids, bone conduction devices, electro-acoustic devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical pressure changes within the cochlea fluid. Such individuals can benefit from implantable auditory prostheses that stimulate nerve cells of the recipient's auditory system in other ways (e.g., electrical, optical and the like). Electro-acoustic devices are often proposed when there is residual acoustic hearing in, for example, the lower frequency ranges that can be utilized for sound perception (e.g., via conventional acoustic amplification), and sound perception can be evoked in the higher frequencies via a cochlear implant. An auditory brainstem stimulator is another type of stimulating auditory prosthesis that might also be proposed when a recipient experiences sensorineural hearing loss due to damage to the auditory nerve.

SUMMARY

In one aspect, a method executed by a hearing prosthesis system is provided. The method comprises: obtaining, at the hearing prosthesis system, a plurality of inner ear potentials associated with an inner ear of a recipient of the hearing prosthesis system; based on the plurality of inner ear potentials, automatically diagnosing, with the hearing prosthesis system, an inner ear crisis affecting the inner ear of the recipient; and in response to diagnosis of the inner ear crisis, automatically initiating one or more remedial actions at the hearing prosthesis system to address the inner ear crisis.

In another aspect, a hearing prosthesis system is provided. The hearing prosthesis system comprises: an intra-cochlear stimulating assembly configured to be implanted in a recipient, wherein the intra-cochlear stimulating assembly comprises a plurality of stimulating contacts; and one or more processors configured to: identify at least one crisis signature from one or more inner ear potentials obtained via the plurality of stimulating contacts; correlate the at least one crisis signature to clinical symptoms of a specific type and cause of an inner ear crisis; and based on the specific type and cause of the inner ear crisis, adjust operation of the hearing prosthesis to remediate the inner ear crisis.

In another aspect, a hearing prosthesis system is provided. The hearing prosthesis system comprises: one or more stimulating contacts configured to be implanted in a recipient and to obtain one or more inner ear potentials at a cochlea of a recipient in response to one or more acoustic or electrical stimulation signals; and an expert diagnosis system configured to: receive inner ear potentials obtained by the one or more stimulating contacts configured; execute a real-time pattern matching process that analyzes various combinations of the inner ear potentials with respect to a database of known relationships between potentials and clinical symptoms to identify an inner ear crisis affecting the cochlea of the recipient; and automatically initiate one or more remedial actions to address the inner ear crisis.

BRIEF DESCRIPTION OF THE DRAWINGS

Embodiments of the present invention are described herein in conjunction with the accompanying drawings, in which.

DETAILED DESCRIPTION

Auditory/hearing prosthesis recipients suffer from different types and levels of hearing loss (e.g., conductive and/or sensorineural). However, it is now common for many hearing prosthesis recipients to retain some residual natural acoustic hearing ability (residual hearing) after receiving the hearing prosthesis. That is, hearing prosthesis recipients often retain at least some of their natural ability to hear sounds. There has been increased focus on preserving a recipient's residual hearing during implantation of a hearing prosthesis into the recipient. For example, in the case of cochlear implants, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the higher frequency regions of the cochlea. Accordingly, greater numbers of recipients have post-implantation residual hearing in an ipsilateral and/or contralateral ear. The benefits of post-implantation residual hearing may include, for example, improved sound localization, music appreciation, binaural release from unmasking, head shadow, and the ability to distinguish acoustic signals in a noisy environment.

However, there is also risk that post-implantation (i.e., after the hearing prosthesis has been implanted within the recipient) problems may affect the health or function of a recipient's inner ear, including the recipient's residual hearing. In certain circumstances, these post-implantation problems, referred to herein as "inner ear crises," could render the recipient's hearing prostheses ineffective. In other cases, continued operation of the hearing prostheses could exacerbate an inner ear crisis. Presently, hearing prostheses lack any ability to monitor, or predict, particularly in an automated or objective manner, the occurrence of inner ear crises. Instead, conventional techniques require a recipient to visit a clinic where the recipient is evaluated by a trained audiologist, clinician, or other hearing professional (collectively and generally referred to herein as "clinicians") typically using complex equipment and procedures. However, recipients do not visit clinics on a regular basis due to, for example, costs, low availability of trained audiologists, such as in rural areas, etc. In certain cases, the change to acoustic hearing for the recipient goes unnoticed due to the inner ear changes being either subtle or of slow progression.

Presented herein are techniques for using an expert diagnosis system integrated in a hearing prosthesis system to diagnosis, grade, and remediate (e.g., initiate treatment of) inner ear crises. In particular, the expert diagnosis system analyzes combinations of in-situ measured inner ear potentials, obtained in response to electrical and/or acoustic stimulation, in order to (1) identify crisis signatures and to (2) correlate those crisis signatures to clinical symptoms of a specific type and cause of an inner ear crises (i.e., automatically diagnosis the inner ear crisis). The expert system is further configured to grade the severity of the identified clinical symptoms and initiate some form of remedial action to address the identified inner ear crisis. The remedial actions are based on the diagnosis of the inner ear crisis and the grade assigned to the diagnosed inner ear crisis. In general, the remedial actions may include any actions intended to negate, minimize or treat the inner ear crisis, including actions to prevent additional damage to the inner ear based on the diagnosis and grading operations. As described further below, the techniques presented herein are substantially automated and can be carried out repeatedly with minimal or no involvement, or possibly even awareness, by the recipient.

For ease of illustration, embodiments are primarily described herein with reference to a hearing prosthesis system that includes an electro-acoustic hearing prosthesis comprising a cochlear implant portion and a hearing aid portion. However, it is to be appreciated that the techniques presented herein may be used with other types of hearing prostheses systems, such as systems that include cochlear implants, direct acoustic stimulators, middle ear implants/stimulators, bone conduction devices, auditory brainstem implants, bi-modal hearing prostheses, and/or electro-acoustic hearing prosthesis comprising other types of output devices (e.g., auditory brainstem stimulators portions, direct acoustic stimulator portions, bone conduction device portions, etc).

Figure 1A:
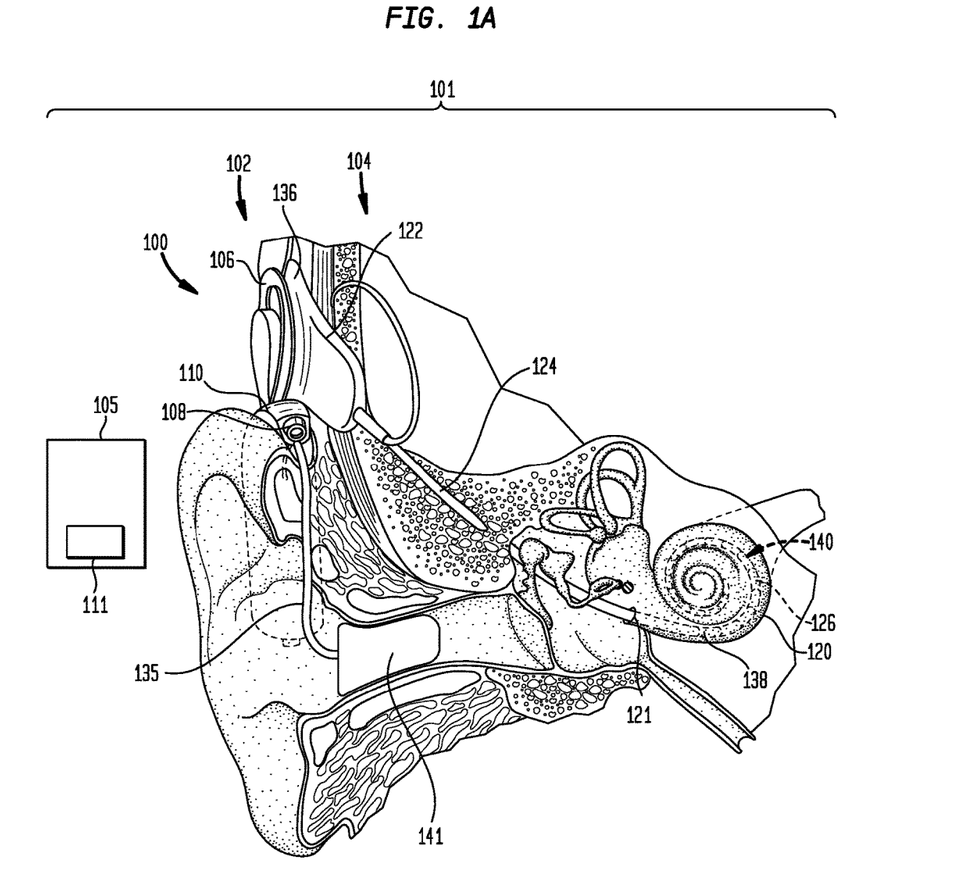
FIG. 1A is a schematic diagram of a hearing prosthesis system in accordance with embodiments presented herein.
Figure 1B:
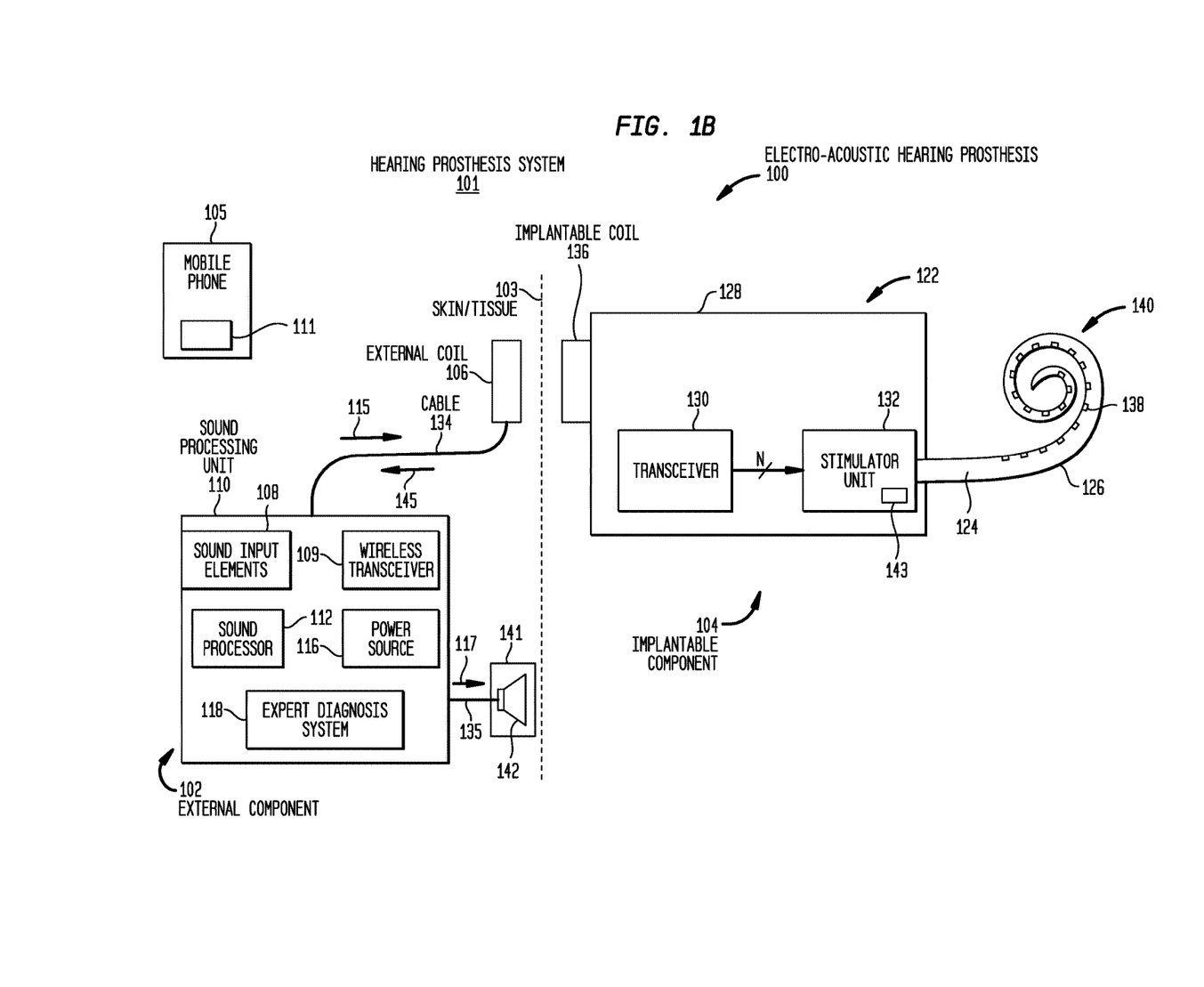
FIG. 1B is a block diagram of the hearing prosthesis system of FIG. 1A.

FIGS. 1A and 1B are diagrams of an illustrative hearing prosthesis system 101 configured to implement the techniques presented herein. More specifically, FIGS. 1A and 1B illustrate hearing prosthesis system 101 that comprises an electro-acoustic hearing prosthesis 100 and an external device 105. The external device 105 is a computing device, such as a computer (e.g., laptop, desktop, tablet), mobile phone, remote control unit, etc. For ease of description, the external device 105 is described as being a mobile phone.

The implantable electro-acoustic hearing prosthesis 100 includes an external component 102 and an internal/implantable component 104. The external component 102 is configured to be directly or indirectly attached to the body of a recipient, while the implantable component 104 is configured to be subcutaneously implanted within the recipient (i.e., under the skin/tissue 103 of the recipient).

The external component 102 comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a wireless transceiver 109, a sound processor 112, a power source 116, and an integrated expert diagnosis system 118. The sound processing unit 110 may be, for example, a behind-the-ear (BTE) sound processing unit, a body-worn sound processing unit, a button sound processing unit, etc.

Connected to the sound processing unit 110 via a cable 135 is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation signals) to the recipient via the recipient's ear canal and middle ear.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intracochlear electrical stimulating contacts (electrodes) 138 that collectively form a contact array 140 for delivery of electrical stimulation (current) to the recipient's cochlea.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured execute sound processing and coding to convert the electrical input signals received from the sound input elements into output signals that represent acoustic and/or electric (current) stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustic stimulation signals to the recipient. As such, depending on a variety of factors, the sound processor 112 is configured to convert the electrical input signals received from the sound input elements into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the encoded data and power signals are received at the transceiver 130 and are provided to the stimulator unit 132. The stimulator unit 132 is configured to utilize the encoded data signals to generate electrical stimulation signals (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least one residual hearing). Therefore, the cochlea of a hearing prosthesis recipient can be acoustically stimulated upon delivery of a sound signal to the recipient's outer ear. In the example of FIGS. 1A and 1B, the receiver 142 is used to provide the acoustic stimulation. That is, the receiver 142 is configured to utilize the output signals 117 to generate acoustic stimulation signals that are provided to the recipient's cochlea via the middle ear bones and oval window, thereby creating waves of fluid motion of the perilymph within the cochlea.

Although FIGS. 1A and 1B illustrate the use of a receiver 142 to deliver acoustic stimulation to the recipient, it is to be appreciated that other types of devices may be used in other embodiments. It is also to be appreciated that embodiments of the present invention may be implemented in other hearing prostheses and other arrangements that that shown in FIGS. 1A and 1B. For example, it is to be appreciated that embodiments of the present invention may be implemented in fully-implantable hearing prostheses in which the sound processor, power supply, etc. are all implanted within a recipient so that the hearing prosthesis may operate, for at least a period of time, without the presence of an external component.

As noted, the electro-acoustic hearing prosthesis 100 also comprises the expert diagnosis system 118. As described further below, the expert diagnosis system 118 is configured to, based on a plurality of inner ear potentials measured in-situ from the recipient's inner ear, diagnose, grade, and remediate post-implantation inner crises that may arise during operation of the hearing prosthesis. As used herein, "inner ear potentials" refer to any voltage potential associated with either the electrical properties of the inner ear or its physiological function and/or potentials obtained via measurements at the inner ear. Potentials of a physiological nature (i.e., potentials relating to the physiological function of the inner ear), include acoustically-induced potentials (e.g., electrocochleography (ECoG) responses) and electrically-induced potentials (e.g., electrically evoked compound action potential (ECAP) responses. Other potentials of a physiological nature are referred to herein as higher evoked potentials, which are potentials related to the brainstem and auditory cortex, inclusive of the electrical auditory brainstem responses (EABR), the middle latency response, and cortical responses. Potentials of a physiological nature are sometimes referred to herein as "physiological potentials." Potentials of electrical nature (i.e., potentials relating to the electrical properties of the inner ear itself or intra-cochlear contacts) include voltage tomography responses, measured impedances (bulk and interface), and/or other forms of electrode (stimulating contact) voltage measurements. Potentials of electrical nature are sometimes referred to herein as "physiological electrical potentials."

As used herein, an ECoG measurement refers to the capture of a set of potentials generated in a recipient's cochlea in response to the delivery of acoustic stimulation to the cochlea. A captured set of potentials (i.e., an ECoG response) may include a plurality of different stimulus related potentials, such as the cochlear microphonic (CM), the cochlear summating potential (SP), the auditory nerve neurophonic (ANN), and the auditory nerve or Compound Action Potential (CAP), which are measured independently or in various combinations.

The cochlear microphonic is an alternating current (AC) voltage that mirrors the waveform of the acoustic stimulus at low, moderate, and high levels of acoustic stimulation. The cochlear microphonic is generated by the outer hair cells of the organ of Corti and is dependent on the proximity of the recording electrode(s) to the stimulated hair cells and the basilar membrane. In general, the cochlear microphonic is proportional to the displacement of the basilar membrane by the travelling wave phenomena.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The auditory nerve neurophonic is a signal recorded from the auditory nerve, while the auditory nerve Action Potential represents the summed response of the synchronous firing of the nerve fibers in response to the acoustic stimuli, and it appears as an alternating current voltage. The auditory nerve Action Potential is characterized by a series of brief, predominantly negative peaks, including a first negative peak (N1) and second negative peak (N2). The auditory nerve Action Potential also includes a magnitude and a latency. The magnitude of the auditory nerve Action Potential reflects the number of fibers that are firing, while the latency of the auditory nerve Action Potential is measured as the time between the onset and the first negative peak (N1).

The primary components of the techniques presented herein, namely diagnosis, grading, and remediation of an inner ear crisis are described further below with reference to method 150 of FIG. 2. For ease of illustration, the method of FIG. 2 is described with reference to the electro-acoustic hearing prosthesis system 101 of FIGS. 1A and 1B.

Figure 2:
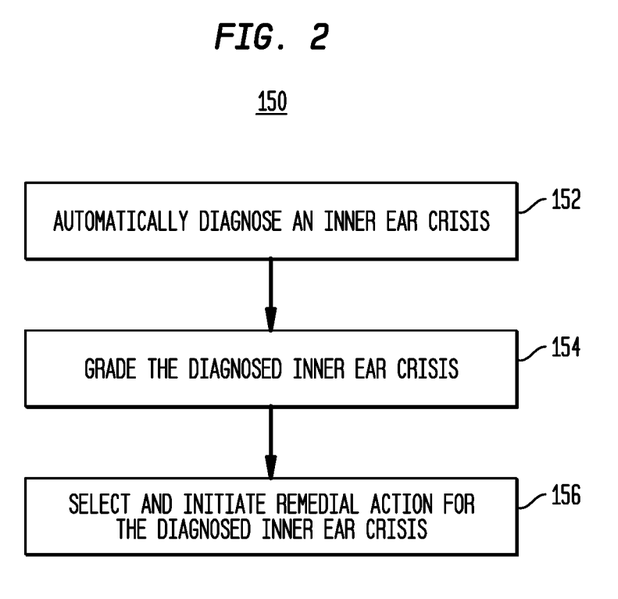
FIG. 2 is a flowchart illustrating automated inner ear diagnosis operations in accordance with embodiments presented herein.

Method 150 of FIG. 2 begins at 152 where the expert diagnosis system 118 is configured to diagnose an inner ear crisis based on in-situ measured inner ear potentials. The measured inner ear potentials are obtained by delivering known electrical and/or acoustic stimulation to the recipient's auditory system, and recording the resulting potentials via the stimulating contacts 138 and one or more amplifiers 143 (FIG. 1B) located in the implantable component 104. In the arrangement of FIGS. 1A and 1B, the measured inner ear potentials, which are generally represented in FIG. 1B by arrow 145, are transmitted back to the external component 102 for storage and subsequent use by the expert diagnosis system 118 (i.e., integrated amplifier of the cochlear implant captures one or more windows of the evoked activity and sends this via telemetry (wirelessly) back to the sound processing unit 110). As noted, the inner ear potentials may include physiological potentials, such as acoustically-evoked potentials (i.e., an ECoG response) and electrically-evoked potentials (e.g., ECAP, EABR, stapedial reflex threshold (ESRT), etc.), and/or physiological electrical potentials (e.g., EVT, impedances, etc.).

The measurement of the inner ear potentials may be initiated by the expert diagnosis system 118. In the case of an acoustically-induced potential measurement, such as an ECoG measurement, the expert diagnosis system 118 is configured to cause the receiver 142 to deliver acoustic stimulation to the recipient's cochlea 120. In the case of an electrically-induced potential measurement and physiological electrical potential measurements, the expert diagnosis system 118 is configured to cause the stimulator unit 132 to deliver electrical stimulation to the recipient's cochlea 120. Following delivery of the acoustic or electrical stimulation, the expert diagnosis system 118 is configured to receive a group/set of inner ear potentials 145. In an embodiment, the inner ear potentials 145 are transmitted from the external coil 106, through the sound processor 112, to the expert diagnosis system 118. In another embodiment, the inner ear potentials 145 are transmitted from the external coil 106 directly to the expert diagnosis system 118.

The inner ear potential measurements may be performed, for example, periodically, at preselected times, in response to user inputs, etc. For example, the measurements may be conducted either at the start of the day or when the recipient first places the external coil 106 on his/her head. Alternatively, the measurements are conducted at times least invasive to the recipient's listening experience. In certain examples, the recipient may be provided with a notification indicating that measurements are about to be performed. Alternatively, the measurements may be conducted at sub-clinical levels that cannot be perceived by the recipient. The measurements may also be inter-dispersed in the clinical operation of the hearing prosthesis such that the measures are not perceived and can be obtained continuously.

As noted, FIGS. 1A, 1B, and FIG. 2 illustrate the use of a receiver 142 to deliver acoustic stimulation for the performance of an acoustically-induced potential measurement. However, embodiments of the present invention may be implemented in other hearing prostheses that deliver stimulation in a different manner to evoke an acoustically-induced potential measurement (e.g., bone conduction devices or direct acoustic stimulators that deliver vibration to the cause pressure changes within the cochlea fluid). It is also to be appreciated that embodiments of the present invention may be implemented in hearing prostheses that do not deliver acoustic stimulation. For example, the cochlea of some hearing prosthesis recipients can be acoustically stimulated upon delivery of a sound signal to the recipient's outer ear without the aid of the hearing prosthesis itself (e.g., recipient's who are implanted with only a cochlear implant). In such recipients, an acoustically-induced potential measurement may be performed in response to the un-aided acoustic stimulation (e.g., via an external acoustic receiver forming part of external device 105 or other external device).

Returning to the specific embodiment of FIG. 2, to diagnose an inner ear crisis, the expert diagnosis system 118 analyzes the inner ear potentials to identify one or more "crisis signatures." As used herein, crisis signatures are combinations of inner ear potentials that, across one or more of frequency, phase, and magnitude, correspond to established/known patterns of inner ear potentials that relate to at least one known pathology, pathophysiology, and/or physiology that correlates to clinical symptoms of a specific "type" of an inner ear crises. In other words, at 152, the expert diagnosis system 118 evaluates, in real-time, various combinations of measured inner ear potentials to identify the presence/occurrence of an inner ear crisis, and to make an informed clinical determination the nature of the inner ear crisis (i.e., classify the inner ear crisis as one of a plurality of different types of crises). Some of the inner ear crisis that may be diagnosed by the expert diagnosis system 118 include, but are not limited to, endolymphatic hydrops, infection or immunological response, conductive hearing loss, progressive hearing loss, atraumatic surgery, etc.

In addition to the identification of the "type" of an inner ear crisis (i.e., the nature of the inner ear crisis), the expert diagnosis system 118 is configured to make an informed clinical determination as to "why" the inner crisis has likely occurred (i.e., determine what is thought to be the underlying cause, including disease or pathophysiological pathway, for the crisis signature observed via the inner ear potentials). That is, at 152, the expert diagnosis system 118 also identifies the underlying reason/cause for the identified inner ear crisis by correlating the inner ear potentials with known information underlying causes of known inner ear crises. For example, a determination of conductive hearing loss may include, or be supplemented by, a determination that conductive hearing loss relates to, for example, fibrosis tissue and/or bone growth in or around the cochlea. The determination extends to biological and immunological processes which can occur post-operatively.

From a functional perspective, the diagnosis performed by the expert diagnosis system 118 at 152 may be viewed as being formed by three operations, namely identification of a crisis signature, determination of the nature of the inner ear crisis corresponding to the crisis signature, and determination of an underlying cause of the inner ear crisis corresponding to the crisis signature. Although these three operations may be viewed as separate functions, in practice some or all of these functions may be performed simultaneously by the expert diagnosis system 118 through the correlation of inner ear potentials with a pattern relating to a known pathology, pathophysiology, and/or physiology of known inner ear crises. In one form, the diagnosis at 152 operates as a real-time pattern recognition/matching algorithm that analyzes various combinations of inner ear potentials with respect to a database of known relationships between potentials and clinical symptoms. Stated differently, the inner ear potentials may be used as inputs to a pattern matching algorithm that correlates various combinations of the inner ear potentials with established patterns. The pattern matching algorithm may be utilized to detect both instantaneous (gross) or longer term changes (i.e., match a discrete set of potentials to another discrete set to detect an instantaneous change or example multiple sets of potentials over time to recognize the occurrence of a long-term change). The database may form part of the expert diagnosis system 118.

The expert diagnosis system 118 may perform the diagnosis, as well as the grading described below, based on a number of different inner ear potentials and/or combinations/permutations of inner ear potentials. However, in one specific embodiment, the diagnosis is based on a combination of acoustically-evoked potentials obtained as part of an ECoG response in combination with one or more physiological electrical potentials, such as impedances.

Returning to the specific example of FIG. 2, after the diagnosis at 152, the method 150 proceeds to 154 where the expert diagnosis system 118 is configured to "grade" the severity of the inner ear crisis. In general, the process of grading the severity of the inner ear crisis will depend on the diagnosis and refers to assigning a rank or rating (e.g., low, medium, and high) to the identified inner ear crisis relative to other inner ear crisis of the same type. That is, the severity of the diagnosed inner ear crisis may be relative to other inner ear crisis of the same nature. The grade may be determined based on a number of factors deduced from the inner ear potentials. In certain examples, the grade may be considered as either a continuous or discrete scale that is the same or different for various diagnoses. The grade of the severity of the inner ear crisis may be used to select at least one of a type or timing of a remedial action based on a grade of the severity of the inner ear crisis.

More specifically, at 156, the expert diagnosis system 118 is configured to use both the diagnosis and the grade to select and initiate some form of remedial action to address the diagnosed inner ear crisis. That is, the expert diagnosis system 118 is configured to enact one or more actions to minimize or treat the inner ear crisis, including actions to prevent additional damage to the inner ear, as needed, based on the diagnosis and grading operations. In certain embodiments, the remedial actions selected and initiated by the expert diagnosis system 118 include automatic alteration of the clinical settings (e.g., selected operating parameters) of the electro-acoustic hearing prosthesis 100 to generate electrical and/or acoustic stimulation signals for delivery to the recipient. The ability to adjust the clinical settings of the electro-acoustic hearing prosthesis 100 to accommodate mild to moderate changes to the hearing profile, thereby minimizing or possibly eliminating the need for the recipient to see a clinician in order to maintain the clinical performance of the prosthesis.

Adjustment to one or more clinical settings used by the electro-acoustic hearing prosthesis 100 to generate the electrical and/or acoustic stimulation signals can include adjustments configured to lessen the intensity and or overlap of the stimulation delivered to the cochlea (e.g., remove or minimize interactions between the electric and acoustic stimulation signals), prevent the incidence of excitotoxicity specific to cochlea sensory structures, minimize or mediate the onset of acoustic hearing loss (and in the event pharmacological agents are employed, optimizing the clinical parameters to complement drug therapy), or detect then prevent the onset of neural fatigue or adaption. Adjustments to clinical parameters controlling electrical stimulation may also include adjustments to sequential clinical parameters (e.g., current level, pulse width, phase extender or third phase, rate or timing, mode, electrode, and frequency to electrode allocation), simultaneous clinical parameters (e.g., phased array parameters), and/or composite stimulation parameters. For example, the hearing prosthesis may reduce the instantaneous current level (CL) delivered to the cochlea by reducing the clinical current level on the electrode in question. In addition, as the charge of the stimulus is dictated by the current level and pulse width (PW), it may be possible to increase the pulse width and reduce the current level to maintain the same perceived loudness, but at the same time reduce the intensity of the stimulus as a remedial therapy to an identified cochlea health change. For stimulation overlap, the hearing prosthesis may either alter the frequency mapping of the acoustic and or electrical stimulus so that the stimulation is delivered to non-overlapping regions of the cochlea. This may be performed using imaging data of the electrode array insertion. Adjustments to clinical settings controlling acoustic stimulation may include adjustments to, for example, applied frequencies (e.g., aidable frequencies and/or compressive frequency allocation), the crossover point/frequency (i.e., the frequency point or range indicating the areas/ranges that receive acoustic or electrical stimulation), sound intensity (e.g., gains, maximum power output, and/or maximum comfort level), and adaptive components (e.g., compression, such as onset, recovery, noise reduction, and/or directionality).

In addition to the monitoring of subtle changes in the cochlea health of the patient, more abrupt or larger scale changes might be monitored and detected in an effort to trigger either a different or more graded intervention. For example, the detection of localized or widespread impedance changes in the cochlea (these may be either at the interface or the bulk between the electrodes) may alert the system to the onset of an innate immunological response in the cochlea, the affects of which might be minimized or negated by the introduction of a corticosteroid for example. Furthermore, the magnitude and the rate of change of the impedance increase or decrease may be employed to either triage or control the rate of the mediation. Other large scale events in the cochlea might be the onset or widespread presence of endolymphatic hydrops within the cochlea, that might be detected by the ratio of the summating and action potential. These wider scale events may be indicative of more global events in the cochlea associated with either different or more mature changes in the cochlea health that can require unique or more diffuse treatment methods.

In certain embodiments, the remedial actions selected and initiated by expert diagnosis system 118 include the triggering of an audible or visual alert to the recipient, caregiver, or other user located in the physical proximity to the hearing prosthesis system (i.e., a local user). The alert may include, for example, information about the identified inner ear crisis, such as the type, cause, grade, etc., and/or recommendations regarding operations to further address the inner ear crisis. The remedial may also include the sending of a "diagnosis notification" to an outside entity such as, for example, a clinic or other medical organization via an automated notification mechanism (e.g., wireless automated notification to a health professional via paired and/or connected communication devices). As used herein, a diagnosis notification is a data message that is transmitted to a remote location and is distinguishable from a message that is delivered to the recipient or local user. As described further below, the diagnosis notification includes information identifying the diagnosis, grade and remediation determined by the expert system 118 (e.g., recommended changes to the clinical settings of the electro-acoustic hearing prosthesis 100, recommendation for delivery of pharmacological agents to the cochlea, etc.).

Certain hearing prostheses include an implantable pump or other system configured to deliver pharmacological agent (e.g., drugs) to the recipient's cochlea. In such prostheses, the remedial actions selected and initiated by expert diagnosis system 118 may include initiation of the administration of a pharmacological agent into or around of the cochlea via the implantable pump or other system. For example, in such embodiments, when the electro-acoustic hearing prosthesis 100 is equipped with a pharmacological agent delivery system (e.g., an infusion pump or an activated drug eluting array), the prosthesis may be configured to not only auto-regulate the clinical stimulus parameters (e.g., to determine if the symptoms abate), but also to administer regulated doses of pharmacological agents, such as corticosteroids, to the recipient's inner ear.

As noted, the expert diagnosis system 118 is configured grade the severity of a diagnosis. The determined severity grade may be used to, for example, select the type of remedial action that is initiated, the timing of the remedial action, etc. For example, the expert diagnosis system 118 may diagnosis inflammation within the recipient's cochlea. The inflammation may then be graded as mild inflammation, moderate inflammation, or severe inflammation. Since mild inflammation may be treated different from severe inflammation, the grading of the diagnosis allows the expert diagnosis system 118 to, in essence, triage the diagnosis and further refine the remedial action that is selected and initiated.

In accordance with embodiments presented herein, once a remedial action (e.g., change in stimulation parameters, delivery of pharmacological agents, etc.) is initiated, the expert diagnosis system 118 may be configured to monitor the efficacy of the remedial action. That is, the expert diagnosis system 118 may continue to analyze inner ear potentials, as described above, to ensure that the remedial action has achieved the underlying target effect. If the remedial action has not achieved the target effect, the expert diagnosis system 118 may initiate one or more additional remedial actions. In certain examples, the failure to achieve a target effect may cause a shut-down of the hearing prosthesis, cause the hearing prosthesis to enter a "safe" mode of operation where, for example, only minimal or critical stimulation is presented to the recipient, or may cause the generation of an alert and/or the transmission of a diagnosis notification.

In certain embodiments presented herein, the expert diagnosis system 118 is configured to identify critical time periods in the life of a recipient that may have increased possibility for damage to the inner ear. As such, the expert diagnosis system 118 may cause the hearing prosthesis to enter an additional mode of operation whereby, for example, applied electrical and/or acoustic stimulation are minimized during such identified time periods. In such examples, the hearing prosthesis may be first enabled either at the clinic or at home with the diagnosis system monitoring the inner ear potentials as the system is being configured clinically. The hearing prosthesis is then configured to ensure that the clinical settings are kept within boundaries defined as non-harmful by the diagnosis system. These clinical settings may be adjusted at later time points during the prosthesis operation when it is determined that the inner ear is less prone to damage.

The embodiments of FIGS. 1A, 1B, and 2 have been described with reference to the expert diagnosis system 118 implemented at sound processing unit 110. That is, FIGS. 1A, 1B, and 2 illustrate an expert diagnosis system that is fully integrated in a hearing prosthesis such that the cochlear response measurement, diagnosis, grading, and selection of remedial actions are all performed by the electro-hearing prosthesis itself. As noted, the sound processing unit 110 may be an external component or the functions of the sound processing unit may be performed by an implantable component (i.e., an implantable sound processing unit). It is to be appreciated that one or more of the operations of the expert diagnosis system 118 may be performed by an external device such that the expert diagnosis system is partially integrated in the hearing prosthesis itself, but still fully integrated in the hearing prosthesis system. For example, in one such partially integrated expert diagnosis system, the inner ear potentials are measured by the hearing prosthesis and then sent to the external device for analysis. The hearing prosthesis may then receive instructions/commands from the external device to initiate one or more remedial actions. In such embodiments, the external device is a local device (e.g., mobile phone, computer, remote control, etc.) that is part of the hearing prosthesis system. In alternative embodiments, one or more operations may be performed by a remote device (e.g., server, computer, etc.).

In certain examples, the information generated by the expert diagnosis system (e.g., the obtained measurements, diagnosis, grad, and selected remedial actions) are all provided to a centralized database (e.g., a cloud database) for use by a centralized analysis engine. That is, a centralized database can collect each new set of data generated by a number of different hearing prostheses so that the analysis engine can adaptively improve the diagnosis process. The expert diagnosis systems on hearing prostheses can receive updates from the centralized analysis engine to improve the ongoing accuracy of the diagnosis and remediation operations, due to the fact that each new recipient will have data on the clinical efficacy of the resulting mediation.

Is there value in stating that the measurements and the results of the interventions (given this is a closed loop system) are stored in the cloud. Each new measurement is added to the analysis engine to improve its ongoing accuracy given each new recipient will have data on the clinical efficacy of the resulting mediation In summary, FIG. 2 illustrates operation of an expert diagnosis system configured for automated remote monitoring (including alerts and automated adjustments) of a recipient's inner ear health based on different inner ear potentials (e.g., acoustically evoked potentials, auditory nerve activity, etc.). The expert system can act to detect and remediate both severe and moderate events that occur in a recipient's inner ear. In the case of severe events, the system has the ability to raise an alarm to the recipient and/or the hearing professional so that, for example, the recipient may be examined urgently to determine if administration of a regime of a pharmacological agent (e.g., steroids) may address the detected event. Furthermore, in the case of moderate changes (acute or progressive), the expert system may initiate automated adjustments to the clinical settings in the hearing prosthesis in order to maintain clinical performance without the need for the recipient to immediately visit a clinic.

It is to be appreciated that there are many use cases for the techniques presented herein. For example, there are cases where a recipient's residual acoustic hearing changes either acutely or progressively following cochlear implant surgery. Overlaying the post-operative change in hearing related to the surgery, can be progressive changes to the residual hearing caused by well-known pathologies such as, for example, ageing, etc. Whether the loss in residual hearing is related to the surgical intervention or via more conventional mechanisms, any change in acoustic hearing, if undetected, poses a significant problem for recipients of electro-acoustic hearing prosthesis. However, it is not uncommon for the loss in the low frequency hearing to go unnoticed by the recipient. This unperceived loss in hearing is likely related to the dominance of the electrical stimulation in the recipient's total perception of sound (i.e., the electrical stimulation is dominates perception, given the wider bandwidth of operation and higher effective audibility of the system).

As described above, in certain embodiments, the techniques presented herein enable an expert diagnosis system forming part of an electro-acoustic hearing prosthesis or electro-acoustic hearing prosthesis system to diagnosis a loss in residual hearing that is experienced by a recipient, even if it is not noticed by the recipient. Also as described above, the expert diagnosis system is configured to grade the hearing loss and to select and initiate remedial action to address the hearing loss. This detection of residual hearing loss and proactive intervention may be particularly relevant in the first twelve (12) months following surgery where it is known that sudden losses to the hearing may occur. Further to this, even in cases where the change to the hearing is minor or moderate, such changes may necessitate changes to the clinical settings of the hearing prosthesis. Again, as noted, an expert diagnosis system in accordance with embodiments present herein may initiate these changes, possibly without the need for a clinical visit or intervention by a hearing profession. The automated detection of residual hearing loss and/or remediation thereof is not possible in conventional hearing prostheses. As a result, without effective detection and treatment strategies, it is not possible for conventional hearing prostheses to prevent or minimize the loss of this residual hearing.

Again, it is to be appreciated that there are many use cases for the techniques presented herein. However, to further illustrate aspects of the present invention, a specific use case is described below with reference to the arrangement of FIGS. 1A and 1B. More specifically, in this specific use case, approximately two (2) weeks after implantation of the electro-acoustic hearing prosthesis 100, the expert diagnosis system 118 detects a cochlear microphonic (CM) to summating potential (SP) ratio (i.e., a inner ear crisis signature) that strongly suggests the onset of an inner ear crisis in the form of endolymphatic hydrops. The expert diagnosis system 118 grades the identified inner ear crisis as significant/severe and automatically initiates a notification to a clinic via an automated notification system (e.g., via a wireless notification sent by transceiver 109). In addition, the expert diagnosis system 118 automatically initiates a reduction in amplification of acoustic stimulation in an effort to minimize trauma and discomfort to the recipient. In other words, the expert diagnosis system 118 initiates two remedial actions in the form of an external notification and a change in the operation of the electro-acoustic hearing prosthesis 100.

When the recipient visits the clinic, systemic steroids are administered to the recipient. After administration of the systemic steroids, the expert diagnosis system 118 continues to monitor the inner ear via measured potentials. As such, the expert diagnosis system 118 is configured to detect if and/or when the hydrodrops abates/subsides (e.g., detecting a change in the CM to SP ratio). In other words, as noted above, the expert diagnosis system 118 is configured to monitor the efficacy of the applied treatment. If the expert diagnosis system 118 determines that the applied has not been effective (e.g., a predetermined period of time has passed without an expected change in the CM to SP ratio), then the expert diagnosis system 118 may initiate one or more additional remedial actions, such as a new notification to a clinic, further changes to operation of the hearing prosthesis 100, etc.

Continuing with the above example, administration of the systemic steroids causes the hydrodrops to subside, which is detected by the expert diagnosis system 118. The expert diagnosis system 118 then notifies the clinic that the hydrodrops have subsided. However, approximately six (6) weeks after implantation of the electro-acoustic hearing prosthesis 100, the expert diagnosis system 118 detects flags a spike in the bulk impedance of the intra-cochlear stimulating contacts 138. This event is graded as severe and, for this reason, the expert diagnosis system 118 automatically initiates a notification to a clinic as a matter of priority via the automated notification system. In addition, the expert diagnosis system 118 automatically initiates one or more adjustments to operational settings of the electro-acoustic hearing prosthesis 100 so as to reduce both the electrical and acoustic stimulation in order to minimize any discomfort for the individual. As such, the expert diagnosis system 118 has again initiated two remedial actions in the form of an external notification and a change in the operation of the electro-acoustic hearing prosthesis 100. When the recipient visits the clinic, corticosteroids are administered.

After administration of the corticosteroids, the expert diagnosis system 118 continues to monitor the inner ear via measured cochlea responses. As such, the expert diagnosis system 118 is configured to detect if and/or when the bulk impedance, for example, decreases to an acceptable level. If the expert diagnosis system 118 determines that administration of the cortical steroids has not been effective, then the expert diagnosis system 118 may initiate one or more additional remedial actions, such as a new notification to a clinic, further changes to operation of the electro-acoustic hearing prosthesis 100, etc. However, in this specific use case, the expert diagnosis system 118 determines that the bulk impedance has decreased to an acceptable level. As such, the clinical settings of the electro-acoustic hearing prosthesis 100 are restored (e.g., automatically, in response to clinician approval, etc.). As noted above, in certain cases measurements and other information obtained by an expert diagnosis system are sent to a centralized database (i.e., the could) for subsequent analysis or to be shared with the clinician/professional who may wish to over-rule the system and act on the measurements observed in their online portal.

Figure 3:
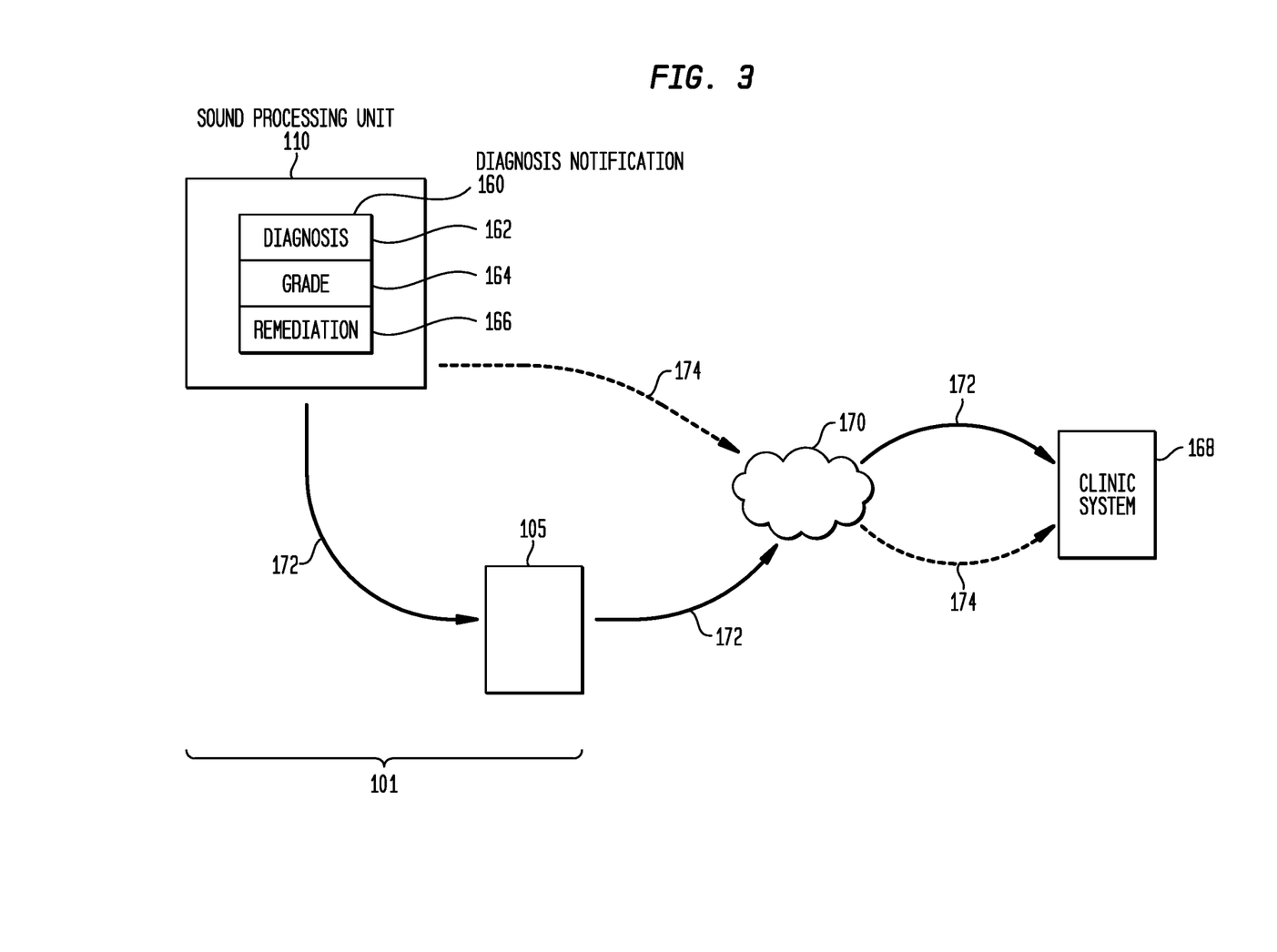
FIG. 3 is a schematic diagram illustrating an automated notification system for diagnosis notifications in accordance with embodiments presented herein.

Continuing further with this example, the expert diagnosis system 118 subsequently diagnoses a loss of residual hearing by the recipient with is graded as moderate. As a result, the expert diagnosis system 118 initiates a modification to the clinical settings associated with acoustic and electrical mapping for the recipient and a notification to a clinic indicating the change. Alternatively, the expert diagnosis system 118 can transmit a notification to a clinic that identifies proposed changes to the clinical settings. A clinician or other hearing professional may then evaluate and approve/modify the proposed changes and initiate a response to the expert diagnosis system 118 with approved changes to the clinical settings. Upon receipt of this message, the expert diagnosis system 118 initiates the approved changes to the clinical settings. In another embodiment, upon identification of the residual hearing loss, a remote or locally administered fitting session may be automatically initiated to determine changes to the clinical settings associated with acoustic and electrical mapping for the recipient As described above, embodiments of the present invention may involve the initiation of remedial actions in the form of diagnosis notifications to an outside entity such as, for example, a clinic or other medical organization via an automated notification mechanism. FIG. 3 is a schematic diagram illustrating an example diagnosis notification and an automated notification mechanism in accordance with embodiments herein.

More specifically, in the example of FIG. 3, a diagnosis notification 160 is generated at sound processing unit 110. As shown, the diagnosis notification 160 includes a diagnosis segment 162, a grading segment 164, and a remediation segment 166. The diagnosis segment 162 includes information describing the clinical diagnosis made by the expert diagnosis system 118, such as an indication of the type of inner ear crisis that has been identified and/or the estimated underlying cause of the inner ear crisis). The grading segment 164 identifies the grade assigned to the inner ear crisis by the expert diagnosis system 118. The remediation segment 166 identifies the remedial actions initiated by, or requested by, the expert diagnosis system 118. For example, the remediation segment 166 may include a request by expert diagnosis system 118 for a clinician to initiate some form of action, such as to administer a remote fitting test.

A diagnosis notification 160 is delivered to an outside entity via an automated notification mechanism. Depending on the capabilities of the sound processing unit 110, the automated notification mechanism may be partially or fully integrated into the sound processing unit 110. FIG. 3 illustrates an embodiment in which the automated notification mechanism comprises an indirect communication channel between the sound processing unit 110 and a clinic system 168.

The communication channel between the sound processing unit 110 and the clinic system 168 is referred to herein as an "indirect" communication channel because the communications are relayed between the sound processing unit 110 and the clinic system 168 via an intermediary device, namely the external device 105. That is, in the specific example of FIG. 3, the sound processing unit 110 lacks the ability to access a telecommunication network or a computing network (i.e., the sound processing unit 110 does not include a telecommunications interface or a network interface). Instead, the wireless transceiver 109 of the sound processing unit 110 is a short-range wireless transceiver configured for wireless communication in accordance with a short-range wireless standard (i.e., over a short-range wireless link/connection). In certain embodiments, the short-range wireless transceiver 109 is a Bluetooth® transceiver that communicates using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. The external device 105 includes a similar wireless transceiver (not shown in FIG. 3). As such, the external device 105 and the sound processing unit 110 communicate over a short-range coupled wireless link/channel.

The external device 105 is a mobile electronic device such as, for example, a remote control device (remote control), a smartphone, etc. The external device 105 has the ability to communicate with the clinic system 168 via one or more network links on a communications network 170 (e.g., a telecommunications network, a wireless local area network, a wide area network, etc.). It is to be appreciated that the clinic system 168 includes one or more components/devices to enable network connectively for communication over communications network 170. Such components are well known in the art and, for ease of illustration, have been omitted from FIG. 3.

Arrows 172 illustrated the path of a diagnosis notification 160 from sound processing unit 110 to clinic system 168 over an indirect communication channel in accordance with embodiments presented herein. That is, arrows 172 collectively illustrate the indirect communication channel that may be used to transfer diagnosis information from expert diagnosis system 118 to a clinic in accordance with embodiments presented herein. As shown, a first portion of the indirect communication channel 172 (i.e., a portion between the intermediary external device 105 and the sound processing unit 110) uses a short-range wireless channel, while a second portion of the indirect communication channel (i.e., a portion between the external device 105 and the clinic system 168) uses one or more telecommunication network links and/or computing network links (e.g., local area networks (LANs), wide area networks (WANs), etc.), collectively and generally referred to herein as network links. As such, the techniques presented herein use the external device 105 as an intermediary relay device (e.g., router/modem) to forward communications between the sound processing unit 110 and the clinic system 168 and vice versa.

The content of the diagnosis notification 160, namely the diagnosis information, grading information, and remediation information, remains as the diagnosis notification is passed over the indirect communication channel 172. However, it is to be appreciated that format of the diagnosis notification 160 may change and that additional information may be added at various portions of the channel. For example, diagnosis notification 160 may have a first packetized format for transmission over the short-range wireless channel from the sound processing unit 110 to the external device 105, but a different packetized format for transmission over the network links between the external device 105 and the clinic system 168.

FIG. 3 has also been described with reference to a specific arrangement in which the diagnosis notification 160 is generated at the sound processing unit 110 and then indirectly forwarded to the clinic system 168 via the external device 105 (i.e., the external device 105 operates as a relay device for the diagnosis notification 160). However, it is to be appreciated that other arrangements are within the scope of the present invention. For example, in another embodiment, the diagnosis notification 160 may be generated at the external device 105, rather than at the sound processing unit 110. In such embodiments, the sound processing unit 110 may send raw data to the external device 105 where the expert diagnosis system 118 is implemented. As such, the external device 105 generates the diagnosis, grading, and remediation information, and, accordingly, generates the diagnosis notification 160.

In another embodiment, the sound processing unit 110 may have the ability to communicate with the clinic system 168 via one or more network links on a communications network 170 (i.e., the sound processing unit 110 includes a wireless local area network interface and/or a telecommunications interface). In these embodiments, a "direct" communication channel is created between the sound processing unit 110 and the clinic system 168, which is represented in FIG. 3 by dashed arrows 174.

The communications described above in FIG. 3 may, in certain examples, be used to upload information obtained by the expert diagnosis system 118 (e.g., measurements, diagnoses, grades, remedial actions, etc.) to a centralized database (e.g., the cloud) for analysis by a centralized system, sometimes referred to herein as a centralized analysis engine. As noted elsewhere herein, the centralized database may receive information from multiple different diagnosis systems in different hearing prostheses that this centrally collected information may be used for various operations by the centralized analysis engine. For example, the expert diagnosis systems on hearing prostheses can receive updates from the centralized analysis engine to improve the ongoing accuracy of the diagnosis and remediation operations, due to the fact that each new recipient will have data on the clinical efficacy of the resulting mediation.

Figure 4:
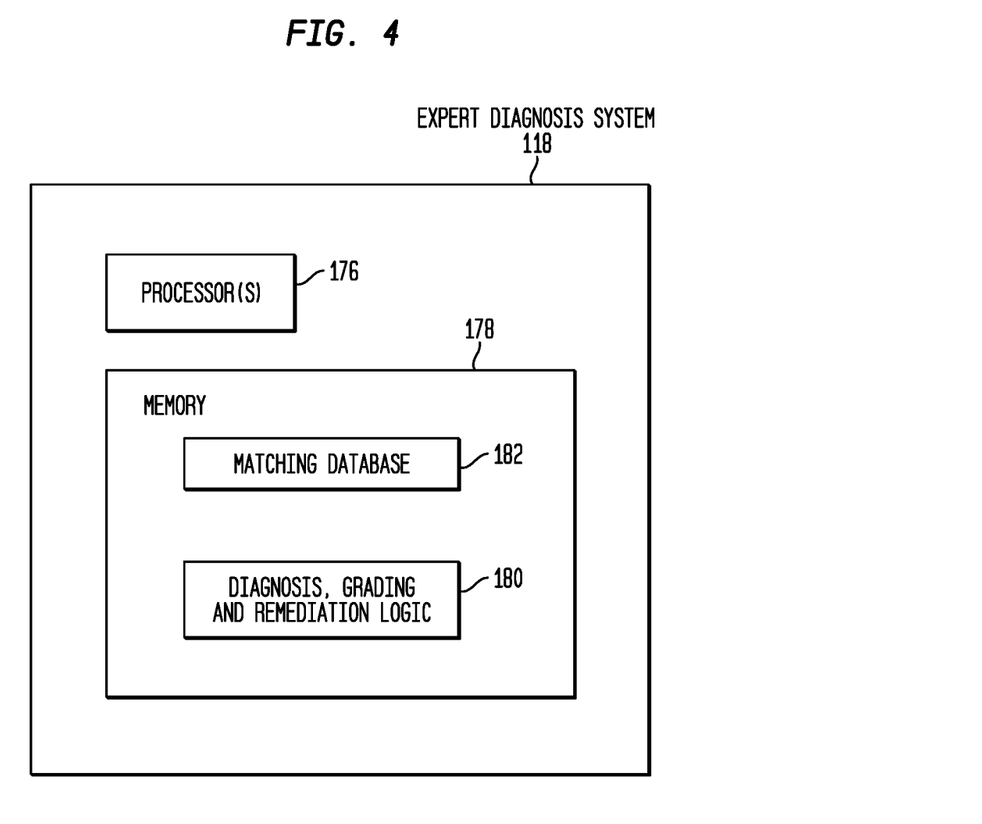
FIG. 4 is a block diagram of an expert diagnosis system in accordance with embodiments presented herein.

FIG. 4 is a schematic block diagram illustrating an arrangement for expert diagnosis system 118 in accordance with an embodiment of the present invention. As shown, the diagnosis system 118 includes one or more processors 176 and a memory 178. The memory 178 includes diagnosis, grading, and remediation logic 180 and a matching database 182.

The memory 178 may be read only memory (ROM), random access memory (RAM), or another type of physical/tangible memory storage device. Thus, in general, the memory 396 may comprise one or more tangible (non-transitory) computer readable storage media (e.g., a memory device) encoded with software comprising computer executable instructions and when the software is executed (by the one or more processors 176) it is operable to perform the operations described herein with reference to expert diagnosis system 118. In particular, the one or more processors 176 execute the diagnosis, grading, and remediation logic 180 to diagnosis and grade an inner ear crisis via pattern matching with information in matching database 182 and to select one or more remedial actions.

FIG. 4 illustrates a specific software implementation for expert diagnosis system 118 that makes use of onboard digital signal processors (DSPs) or microprocessors. However, it is to be appreciated that expert diagnosis system 118 may have other arrangements. For example, expert diagnosis system 118 may be partially or fully implemented with digital logic gates in one or more application-specific integrated circuits (ASICs). Alternatively, the one or more processors 178 of expert diagnosis system 118 may be the same or different processor as the sound processor 112 (FIGS. 1A and 1B).

Figure 5:
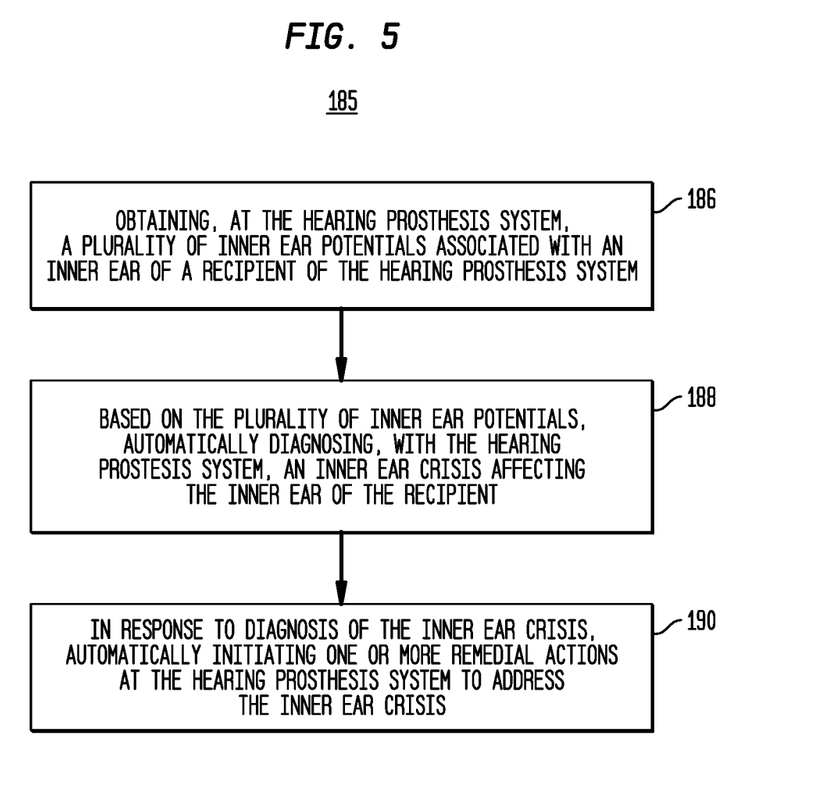
FIG. 5 is a flowchart of a method in accordance with embodiments presented herein.

FIG. 5 is a flowchart of a method 185 in accordance with embodiments presented herein. Method 185 begins at 186 where a hearing prosthesis system obtains a plurality of inner ear potentials associated with an inner ear of a recipient of the hearing prosthesis system. At 188, based on the plurality of inner ear potentials, the hearing prosthesis system automatically diagnoses an inner ear crisis affecting the inner ear of the recipient. At 190, in response to diagnosis of the inner ear crisis, the hearing prosthesis system initiates one or more remedial actions to address the inner ear crisis.

As noted above, embodiments presented herein make use of cochlear potential measurements made within a recipient's hearing prosthesis system in order to diagnosis, grade, and initiate remediation of inner ear crises. Such integration permits remote monitoring of the recipient's inner ear function/health (e.g., monitoring of residual hearing) via the analysis of the electric potentials of the cochlea and the auditory nerve during everyday use of the hearing prosthesis system. In operation, the inner ear potentials are telemetered wirelessly to a sound processing unit that houses an number of digital signal processors (DSPs) capable of analyzing, in real-time, the acquired inner ear potentials. As described further below, based on specific signal characteristics, the hearing prosthesis system diagnoses an inner ear crisis, grades the inner ear crisis, and initiates (triggers) one or more remedial actions, such as an alarm, the transmission of or instigate an automated change in the clinical settings or signal processing, based on the diagnosis and grade. The techniques presented herein do not involve recipient interactions and/or behavioral feedback, but rather may be substantially automated.

For ease of illustration, embodiments have primarily been described herein with reference to one specific type of hearing prosthesis, namely an electro-acoustic hearing prosthesis comprising a cochlear implant portion and a hearing aid portion. However, it is to be appreciated that the techniques presented herein may be used with other types of hearing prostheses, such as cochlear implants, direct acoustic stimulators, middle ear implants/stimulators, bone conduction devices, auditory brainstem implants, bi-modal hearing prostheses, and/or electro-acoustic hearing prosthesis comprising other types of output devices (e.g., auditory brainstem stimulators portions, direct acoustic stimulator portions, bone conduction device portions, etc.). For hearing prostheses without a cochlear implant portion (i.e., without one or more intra-cochlear stimulator contacts), the prostheses may include an electrode or contact placed near the round window of the cochlea to detect the inner ear potentials.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method executed by a hearing prosthesis system, comprising:
   obtaining, at the hearing prosthesis system, a plurality of inner ear potentials associated with an inner ear of a recipient of the hearing prosthesis system;
   based on the plurality of inner ear potentials, automatically identifying, with the hearing prosthesis system, an inner ear crisis indicative of a post-implantation change in health or function of the inner ear of the recipient;
   determining a type of the of the inner ear crisis;
   determining an underlying cause of the inner ear crisis; and
   automatically performing one or more remedial actions at the hearing prosthesis system to address the inner ear crisis,
   wherein the one or more remedial actions are selected at least in part based on the type and underlying cause of the inner ear crisis.

2. The method of claim 1, further comprising:
   grading a severity of the inner ear crisis relative to known inner ear crisis of the same type.

3. The method of claim 2, further comprising:
   selecting at least one of a type or timing of at least one of the one or more remedial actions based on a grade of the severity of the inner ear crisis.

4. The method of claim 1, wherein automatically identifying, with the hearing prosthesis system, an inner ear crisis comprises:
executing a real-time pattern matching process that analyzes various combinations of inner ear potentials with respect to a database of known relationships between potentials and clinical symptoms.

5. The method of claim 1, wherein the hearing prosthesis system includes a hearing prosthesis that delivers electrical and acoustic stimulation signals to the recipient, and wherein initiating one or more remedial actions comprises:
adjusting one or more clinical settings controlling generation of the electrical or acoustic stimulation signals to remediate the inner ear crisis.

6. The method of claim 1, wherein performing one or more remedial actions comprises:
triggering an audible or visual alert to the recipient, caregiver, or other user located in the physical proximity of the hearing prosthesis system.

7. The method of claim 1, wherein performing one or more remedial actions comprises:
sending a diagnosis notification to a remote location, wherein the diagnosis notification comprises type, cause, and remediation information for the inner ear crisis.

8. The method of claim 1, wherein obtaining the plurality of inner ear potentials associated with a cochlea of a recipient of the hearing prosthesis comprises:
performing an electrocochleography measurement to obtain one or more acoustically-induced inner ear potentials.

9. The method of claim 8, wherein obtaining the plurality of inner ear potentials associated with a cochlea of a recipient of the hearing prosthesis further comprises:
performing one or more measurements to obtain one or more physiological electrical inner ear potentials.

10. The method of claim 9, wherein automatically identifying, with the hearing prosthesis system, an inner ear crisis comprises:
analyzing the one or more acoustically-induced inner ear potentials in combination with the one or more physiological electrical inner ear potentials.

11. A hearing prosthesis system, comprising:
an intra-cochlear stimulating assembly configured to be implanted in a recipient, wherein the intra-cochlear stimulating assembly comprises a plurality of electrodes; and
one or more processors configured to:
identify at least one crisis signature from one or more inner ear potentials obtained via the plurality of electrodes,
correlate the at least one crisis signature to clinical symptoms of a specific type and cause of an inner ear crisis indicative of a post-implantation change in health or function of the inner ear, and
based on the specific type and cause of the inner ear crisis, adjust operation of the hearing prosthesis to remediate the inner ear crisis.

12. The hearing prosthesis system of claim 11, wherein the one or more processors are configured to:
grade a severity of the relative to known inner ear crisis of the same type,
wherein the operation of the hearing prosthesis is adjusted based on a grade of the severity of the inner ear crisis.

13. The hearing prosthesis system of claim 11, wherein to correlate the at least one crisis signature to clinical symptoms of a specific type and cause of an inner ear crisis, the one or more processors are configured to:
execute a real-time pattern matching process that correlates various combinations of the inner ear potentials with established patterns.

14. The hearing prosthesis system of claim 11, wherein the hearing prosthesis system including a hearing prosthesis that delivers electrical and acoustic stimulation signals to the recipient, and wherein to adjust operation of the hearing prosthesis to remediate the inner ear crisis the one or more processors are configured to:
adjust one or more clinical settings controlling generation of the electrical or acoustic stimulation signals to remediate the inner ear crisis.

15. The hearing prosthesis system of claim 11, wherein the one or more processors are further configured to:
trigger an audible or visual alert to the recipient, caregiver, or other user located in the physical proximity of the hearing prosthesis system.

16. The hearing prosthesis system of claim 11, wherein the one or more processors are further configured to:
send a diagnosis notification to a remote location, wherein the diagnosis notification identifies the specific type and cause of the inner ear crisis.

17. The hearing prosthesis system of claim 16, wherein the diagnosis information further includes information indicating a severity of the inner ear crisis.

18. The hearing prosthesis system of claim 11, wherein the one or more processors are configured to:
initiate an electrocochleography measurement to obtain one or more acoustically-induced inner ear potentials.

19. The hearing prosthesis system of claim 18, wherein the one or more processors are configured to:
initiate one or more measurements to obtain one or more physiological electrical inner ear potentials.

20. The hearing prosthesis system of claim 19, wherein the one or more processors are configured to identify at least one crisis signature based on the one or more acoustically-induced inner ear potentials in combination with the one or more physiological electrical inner ear potentials.

21. The hearing prosthesis system of claim 11, further comprising:
an implantable hearing prosthesis having a sound processing unit; and
an external device,
wherein the one or more processors are disposed in the sound processing unit of the hearing prosthesis.

22. A hearing prosthesis system, comprising:
one or more electrodes configured to be implanted in a recipient and to obtain one or more inner ear potentials at a cochlea of a recipient in response to one or more or more acoustic or electrical stimulation signals; and
an expert diagnosis system configured to:
receive inner ear potentials obtained by the one or more electrodes configured;
execute a real-time pattern matching process that analyzes various combinations of the inner ear potentials with respect to a database of known relationships between potentials and clinical symptoms to identify: an inner ear crisis associated with a change in health or function of the cochlea of the recipient, type of the of the inner ear crisis, and an underlying cause of the inner ear crisis; and
automatically perform, based on the type of the of the inner ear crisis and the underlying cause of the of the inner ear crisis, one or more remedial actions to address the inner ear crisis.

23. The hearing prosthesis system of claim 22, wherein the expert diagnosis system is configured to grade a severity of the inner ear crisis.

24. The hearing prosthesis system of claim 22, wherein the expert diagnosis system is configured to adjust one or more clinical settings of the hearing prosthesis system to remediate the inner ear crisis.

* * * * *